(12) United States Patent
Song et al.

(10) Patent No.: US 9,897,526 B2
(45) Date of Patent: Feb. 20, 2018

(54) VACUUM APPARATUS AND METHOD OF MONITORING PARTICLES

(71) Applicant: Samsung Display Co., Ltd., Yongin (KR)

(72) Inventors: Eun-Ju Song, Cheonan-si (KR); Hoonchul Ryoo, Asan-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 864 days.

(21) Appl. No.: 14/453,228

(22) Filed: Aug. 6, 2014

(65) Prior Publication Data

US 2015/0198516 A1  Jul. 16, 2015

(30) Foreign Application Priority Data

Jan. 14, 2014  (KR) .......................... 10-2014-0004710

(51) Int. Cl.
| | |
|---|---|
| *G01N 15/06* | (2006.01) |
| *G01L 21/22* | (2006.01) |
| *G01N 29/24* | (2006.01) |
| *G01N 15/00* | (2006.01) |

(52) U.S. Cl.
CPC .......... *G01N 15/0606* (2013.01); *G01L 21/22* (2013.01); *G01N 15/0656* (2013.01); *G01N 29/2443* (2013.01); *G01N 2015/0046* (2013.01); *G01N 2291/0256* (2013.01); *G01N 2291/02408* (2013.01); *G01N 2291/02872* (2013.01)

(58) Field of Classification Search
CPC .......... G01N 15/0606; G01N 15/0656; G01N 29/2443; G01L 21/22
USPC .................................................... 73/575, 572
See application file for complete search history.

(56) References Cited

U.S. PATENT DOCUMENTS

| | | | | |
|---|---|---|---|---|
| 5,618,493 A | * | 4/1997 | Goldstein | G01N 21/77 422/401 |
| 6,569,236 B1 | * | 5/2003 | Morimoto | C30B 15/14 117/14 |
| 7,927,558 B2 | * | 4/2011 | Kirollos | G01N 33/0063 2/457 |
| 8,182,861 B2 | | 5/2012 | Lee et al. | |
| 2011/0022353 A1 | | 1/2011 | Wudy et al. | |
| 2014/0238105 A1 | * | 8/2014 | Sou | H01L 51/56 73/23.2 |

FOREIGN PATENT DOCUMENTS

| | | |
|---|---|---|
| JP | 2004-263985 | 9/2004 |
| JP | 2005-317900 | 11/2005 |
| KR | 10-2005-0072165 | 7/2005 |
| KR | 10-2006-0036771 | 5/2006 |

* cited by examiner

*Primary Examiner* — Hezron E Williams
*Assistant Examiner* — Tarun Sinha
(74) *Attorney, Agent, or Firm* — H.C. Park & Associates, PLC

(57) ABSTRACT

A vacuum apparatus includes a vacuum chamber, first sensor units disposed in the vacuum chamber facing a deposition direction of particles, and second sensor units disposed in the vacuum chamber, each disposed on a corresponding first sensor of the first sensor units facing the deposition direction, wherein the first sensor units are configured to sense a pressure in the vacuum chamber and an absorption amount of the particles adsorbed to the first sensor units, and the second sensor units are configured to sense the pressure in the vacuum chamber.

19 Claims, 4 Drawing Sheets

VACUUM APPARATUS AND METHOD OF MONITORING PARTICLES

CROSS-REFERENCE TO RELATED APPLICATION

This U.S. non-provisional patent application claims priority from and the benefit of Korean Patent Application No. 10-2014-0004710, filed on Jan. 14, 2014, which is hereby incorporated by reference for all purposes as if fully set forth herein.

BACKGROUND

Field

The present disclosure relates to a vacuum apparatus and a method of monitoring particles.

Discussion of the Background

In general, various vacuum processes, such as a deposition process, a sputtering process, a chemical vapor deposition process, an etching process, etc., have been used to manufacture electronic devices. The vacuum processes are performed using a vacuum apparatus. Various equipment and objects may be installed in the vacuum apparatus.

For instance, the vacuum apparatus, in which the deposition process is performed, includes a vacuum chamber, and a substrate and a deposition source, disposed in the vacuum chamber. The substrate and the deposition source are disposed facing each other, and a deposition material evaporated from the deposition source is deposited onto the substrate.

Particles (or contaminant materials) may be generated during the various vacuum processes and exist in the vacuum chamber. As the amount of the particles generated during the vacuum processes increases, a possibility that the particles scattered in the vacuum chamber be attached to the electronic devices becomes high. When the particles are attached to the electronic devices, a reliability of the electronic devices may be decreased. Accordingly, monitoring of the particles generated during the vacuum processes and measuring of contamination levels in the vacuum chamber are required.

The above information disclosed in this Background section is only for enhancement of understanding of the background of the invention and therefore it may contain information that does not form any part of the prior art nor what the prior art may suggest to a person of ordinary skill in the art.

SUMMARY

Exemplary embodiments of the present disclosure provide a vacuum apparatus capable of monitoring particles generated during processes and measuring contamination levels thereof in real time.

Exemplary embodiments of the present disclosure also provide a method of monitoring the particles using the vacuum apparatus.

Additional features of the invention will be set forth in the description which follows, and in part will be apparent from the description, or may be learned by practice of the invention.

Exemplary embodiment of the present inventive concept provides a vacuum apparatus including a vacuum chamber, first sensor units disposed in the vacuum chamber facing a deposition direction of particles, and second sensor units disposed in the vacuum chamber, each disposed on a corresponding first sensor of the first sensor units facing the deposition direction, wherein the first sensor units are configured to sense a pressure in the vacuum chamber and an absorption amount of the particles adsorbed to the first sensor units, and the second sensor units are configured to sense the pressure in the vacuum chamber.

Exemplary embodiment of the present inventive concept also provides a method of monitoring particles in a vacuum apparatus, including sensing a pressure in a vacuum chamber and an absorption amount of the particles adsorbed to first sensor units using the first sensor units, sensing the pressure in the vacuum chamber using second sensor units, and analyzing a contamination level of the vacuum chamber.

According to the above, the vacuum apparatus may monitor the particles generated during the vacuum process and measure the contamination state in the vacuum chamber in real time.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

The above and other advantages of the present disclosure will become readily apparent by reference to the following detailed description when considered in conjunction with the accompanying drawings.

DETAILED DESCRIPTION OF THE ILLUSTRATED EMBODIMENTS

Figure 1:
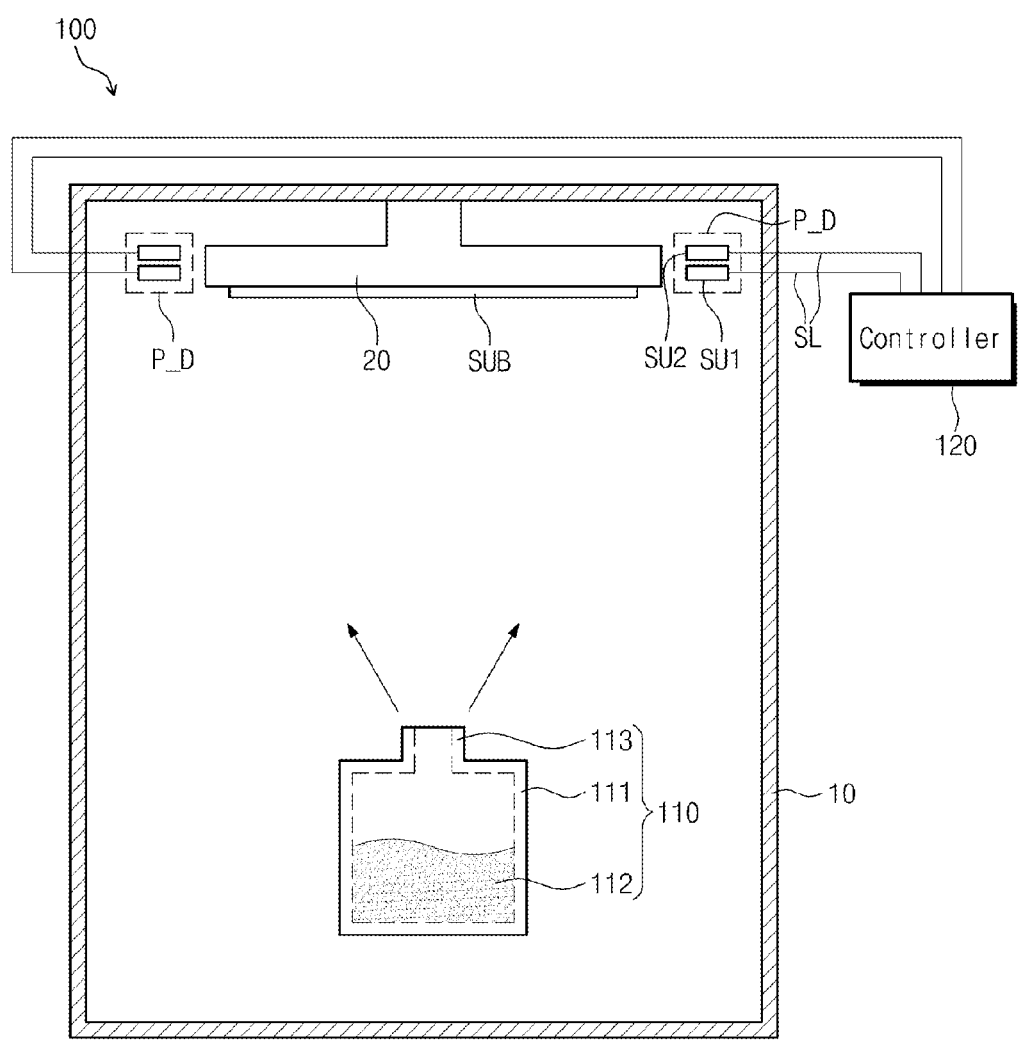
FIG. 1 is a cross sectional view showing a vacuum apparatus according to an exemplary embodiment of the present disclosure.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure is thorough, and will fully convey the scope of the invention to those skilled in the art. In the drawings, the size and relative sizes of layers and regions may be exaggerated for clarity Like reference numerals in the drawings denote like elements.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numbers refer to like elements throughout. As used herein, the term "and/or" includes any and all combinations of one or more of the associated listed items. It will be understood that for the purposes of this disclosure, "at least one of X, Y, and Z" can be construed as X only, Y only, Z only, or any combination of two or more items X, Y, and Z (e.g., XYZ, XYY, YZ, ZZ).

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, the present invention will be explained in detail with reference to the accompanying drawings.

FIG. 1 is a cross sectional view showing a vacuum apparatus 100 according to an exemplary embodiment of the present disclosure.

Referring to FIG. 1, the vacuum apparatus 100 includes a vacuum chamber 10, a deposition source 110, a substrate SUB, a plurality of particle detectors P_D, and a controller 120. For example, the vacuum apparatus 100 may be a vacuum apparatus used for a deposition process.

The vacuum chamber 10 maintains a high vacuum state to prevent foreign substances from entering thereinto and to secure directivity of a deposition material.

The deposition source 110 is disposed at a lower portion in the vacuum chamber 10. For explanation purpose, only one deposition source 110 is shown in FIG. 1, but the number of the deposition source 110 is not limited thereto. Plural deposition sources may be arranged in a line.

The deposition source 110 includes a crucible 111, a deposition material 112, and a nozzle 113. The deposition material 112 is filled in the crucible 111. The nozzle 113 is disposed on an upper surface of the deposition source 110. The deposition material 112 is evaporated in the crucible 111 and sprayed to the substrate SUB through the nozzle 113.

The deposition source 110 is filled with the deposition material 112 which may include an organic material and a metal material to be deposited onto the substrate SUB. The deposition source 110 evaporates the deposition material 112 and sprays the evaporated deposition material to the substrate SUB. The deposition material is sprayed upwardly toward the substrate SUB. The deposition source 110 may further include a heater disposed in the crucible 111 to evaporate the deposition material 112 filled in the crucible 111.

The substrate SUB is disposed at an upper portion in the vacuum chamber 10 facing the deposition source 110. The substrate SUB may be fixed to the upper portion in the vacuum chamber 10 by a substrate supporter 20.

The particle detectors P_D are disposed at the upper portion in the vacuum chamber 10 adjacent to a side surface of the substrate SUB, but they are not limited thereto. The particle detectors P_D may be disposed on an inner wall of the vacuum chamber 10 between the substrate SUB and the deposition source 110.

Referring to FIG. 1, a cross section of the vacuum chamber 10 shows two particle detectors P_D. However, the vacuum chamber 10 may include two or more particle detectors P_D arranged therein.

For instance, when the substrate SUB has a rectangular shape, four particle detectors P_D may be disposed adjacent to four sides of the substrate SUB, respectively, but the number of the particle detectors P_D is not limited to four.

Each of the particle detectors P_D includes a first sensor unit SU1 and a second sensor unit SU2. The second sensor unit SU2 is disposed on top of the first sensor unit SU1.

During a vacuum process, contamination materials, e.g., particles, may be generated in the vacuum chamber 10. For instance, the deposition material 112 sprayed from the deposition source 110 may travel to the areas where the substrate SUB does not exist. The deposition material 112 not provided to the substrate SUB may constitute the particles as the contamination materials.

The particles are provided to the particle detectors P_D disposed adjacent to the substrate SUB. The first sensor unit SU1 is disposed facing a deposition direction of the particles generated during the vacuum process. For instance, a first sensor S1 is disposed at a lower portion of the first sensor unit SU1 and disposed facing the deposition direction of the particles.

Since the deposition material 112 is sprayed onto the substrate SUB and the particles are generated by the deposition material 112 not provided to the substrate SUB, the deposition direction of the particles may be the same as that of the sprayed deposition material.

The second sensor unit SU2 is disposed facing away from the deposition direction of the particles, i.e., the first sensor unit SU1 is disposed between the deposition source 110 and the second sensor unit SU2. For instance, a second sensor S2 is disposed at an upper portion of the second sensor unit SU2. The second sensor S2 is disposed facing away from the deposition direction of the particles.

The second sensor unit SU2 is disposed so that a rear surface thereof is facing a rear surface of the first sensor unit SU1. For instance, an upper surface of the first sensor unit SU1, on which the first sensor S1 is not disposed, may be referred to as the rear surface of the first sensor unit SU1. A lower surface of the second sensor unit SU2, on which the second sensor S2 is not disposed, may be referred to as the rear surface of the second sensor unit SU2. The rear surface of the second sensor unit SU2 faces the rear surface of the first sensor unit SU1. This will be described in detail later with reference to FIG. 2.

The deposition material 112 filled in the crucible 111 is evaporated by heat of the heater disposed inside the crucible 111. The deposition material 112 evaporated from the crucible 111 is sprayed through the nozzle 113. The deposition material 112 sprayed through the nozzle 113 is deposited on the substrate SUB, and thus electronic devices are formed on the substrate SUB.

The first sensor units SU1 sense a pressure in the vacuum chamber 10 and an absorption amount of the particles. The second sensor units SU2 sense a pressure in the vacuum chamber 10.

Information about the pressure of the vacuum chamber 10 and the absorption amount of the particles sensed by the first sensor units SU1 may be applied to the controller 120 in real time through a signal line SL. Information about the pressure in the vacuum chamber 10 sensed by the second sensor units SU2 may be applied to the controller 120 in real time through a signal line SL.

The controller 120 calculates the absorption amount of the particles using the information about the pressure in the vacuum chamber 10 and the absorption amount of the particles sensed by the first sensor units SU1 and the information about the pressure in the vacuum chamber 10 sensed by the second sensor units SU2.

In detail, the controller 120 converts the information about the pressure in the vacuum chamber 10 and the absorption amount of the particles sensed by the first sensor units SU1 to a first data. Also, the controller 120 converts the information about the pressure in the vacuum chamber 10 sensed by the second sensor units SU2 to a second data.

The controller 120 subtracts the second data about the pressure in the vacuum chamber 10 sensed by the second sensor units SU2 from the first data about the pressure in the vacuum chamber 10 and the absorption amount of the particles sensed by the first sensor units SU1 to generate a third data. The third data may correspond to the absorption amount of the particles sensed by the first sensor units SU1 is generated.

The controller 120 may analyze the contamination state in the vacuum chamber 10 using the third data corresponding to the absorption amount of the particles sensed by the first sensor units SU1. For instance, as the absorption amount of the particles increases, the controller 120 determines that the contamination level is high. That is, the controller 120 determines that the contamination level is high when the value of the third data is greater than reference or threshold value.

Therefore, the contamination state of the vacuum chamber 10 may be checked using the pressure in the vacuum chamber 10 and the absorption amount of the particles sensed by the first sensor unit SU1 and second sensor unit SU2.

Consequently, the vacuum apparatus 100 may monitor the particles generated during the vacuum process and measure the contamination state in the vacuum chamber 10 in real time.

Figure 2:
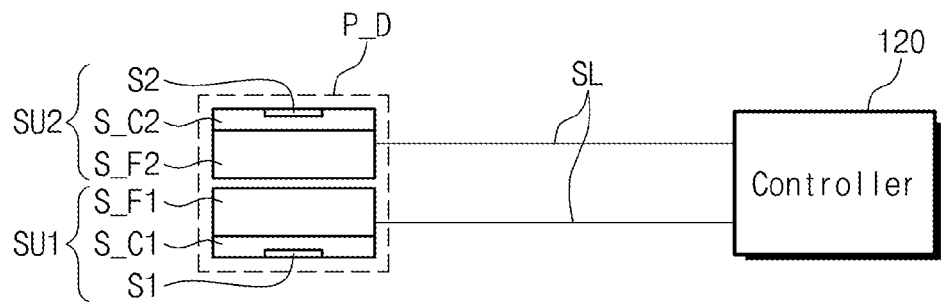
FIG. 2 is a view showing a configuration of a particle detector shown in FIG. 1.
Figure 3:
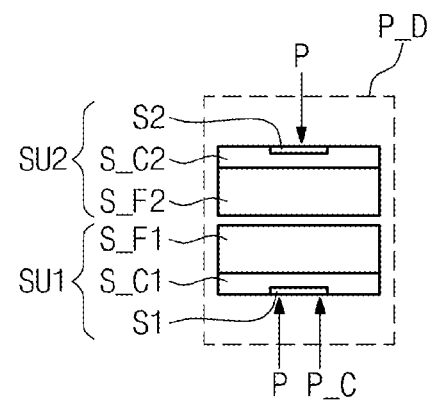
FIG. 3 is a view showing a pressure applied to the particle detector shown in FIG. 2 and particles.

FIG. 2 is a view showing a configuration of the particle detector shown in FIG. 1 and FIG. 3 is a view showing a pressure applied to the particle detector shown in FIG. 2 and particles. FIG. 2 shows an exemplary embodiment of particle detectors P_D, and the particle detectors may have the same configuration and function illustrated in FIG. 2.

Referring to FIGS. 2 and 3, the particle detector P_D includes the first sensor unit SU1 and the second sensor unit SU2. The first sensor unit SU1 includes a first sensor fixture S_F1, a first sensor case S_C1, and the first sensor S1. The first sensor S1 is disposed in the first sensor case S_C1. The first sensor S1 is disposed facing the deposition direction of the particles P_C. The first sensor S1 may be, but not limited to, a crystal vibrator.

The first sensor case S_C1, in which the first sensor S1 is disposed, is disposed under the first sensor fixture S_F1 and fixed to the first sensor fixture S_F1. An upper surface of the first sensor fixture S_F1, which is the opposing surface that the first sensor case S_C1 is disposed, may be defined as a rear surface of the first sensor fixture S_F1. The first sensor fixture S_F1 is connected to the controller 120 through the signal line SL.

The second sensor unit SU2 includes a second sensor fixture S_F2, a second sensor case S_C2, and the second sensor S2. The second sensor S2 is disposed in the second sensor case S_C2. The second sensor S2 is disposed facing away from the deposition direction of the particles P_C. That is, the second sensor S2 is disposed facing the upper direction. The second sensor S2 may be, but not limited to, the crystal vibrator.

The second sensor case S_C2, in which the second sensor S2 is disposed, is disposed above the second sensor fixture S_F2 and fixed to the second sensor fixture S_F2. The lower portion of the second sensor fixture S_F2, which is the opposing surface that the second sensor case S_C2 is not disposed, may be defined as the rear surface of the second sensor fixture S_F2. The rear surface of the second sensor fixture S_F2 is disposed facing the rear surface of the first sensor fixture S_F1. The second sensor fixture S_F2 is connected to the controller 120 through the signal line SL.

The vacuum chamber 10 maintains the high vacuum state, but a pressure P may exist in the vacuum chamber 10. The pressure P of the vacuum chamber 10 exists in all direction inside the vacuum chamber 10. Thus, the pressure P is applied to the first sensor S1 of the first sensor unit SU1 and the second sensor S2 of the second sensor unit SU2 as shown in FIG. 3.

Since the first sensor S1 of the first sensor unit SU1 is disposed facing the deposition direction of the particles P_C, the particles P_C are provided to the first sensor S1 as shown in FIG. 3.

The first and second sensors S1 and S2 may include the crystal vibrator. The crystal vibrator senses the pressure P in the vacuum chamber 10 and the amount of the particles P_C adsorbed to the surface of the crystal vibrator by taking the pressure P in the vacuum chamber 10 and the particles P_C adsorbed to the surface of the crystal vibrator into consideration.

For instance, the number of vibrations, e.g., a frequency, of the crystal vibrator may change by the pressure P. In detail, as the pressure P increases, the frequency of the crystal vibrator may decrease. When the particles P_C are adsorbed to the surface of the crystal vibrator, the frequency of the crystal vibrator may change. In detail, as the amount of the particles P_C adsorbed to the surface of the crystal vibrator increases, the frequency of the crystal vibrator may decrease.

Accordingly, the frequency of the first sensor S1 may be changed depending on the pressure P and the absorption amount of the particles P_C. The change in frequency of the first sensor S1 is provided to the controller 120 in real time through the signal line SL connected to the first sensor fixture S_F1.

The frequency of the second sensor S2 may be changed by the pressure P. The change in frequency of the second sensor S2 is provided to the controller 120 in real time through the signal line SL connected to the second sensor fixture S_F2.

The controller 120 may receive information about the changes in the frequency of the first sensor S1 and the second sensor S2 and calculate the absorption amount of the particles P_C. In detail, the controller 120 converts the change in the frequency of the first sensor S1 caused by the pressure P and the absorption amount of the particles P_C to the first data. The controller 120 converts the change in the frequency of the second sensor S2 caused by the pressure P to the second data.

The controller 120 subtracts the second data from the first data to generate the third data. That is, the third data is obtained by subtracting the second data, which is about the pressure P, from the first data, which is about the pressure P and the absorption amount of the particles P_C. Therefore, the third data may be data indicating the absorption amount of the particles P_C. That is, the third data has a value corresponding to the absorption amount of the particles P_C.

The controller 120 analyzes the contamination state in the vacuum chamber 10 using the third data corresponding to the absorption amount of the particles P_C sensed by the first sensor S1. For instance, as the absorption amount of the particles P_C increases, the controller 120 determines that the contamination level in the vacuum chamber 10 is high. That is, as the value of the third data is greater than reference or threshold value, the contamination level in the vacuum chamber is high.

Thus, the contamination state of the vacuum chamber 100 may be measured using the information about the pressure in the vacuum chamber 10 and the absorption amount of the particles P_C, which are sensed by the first and second sensors S1 and S2.

Compared to the exemplary embodiment of the present invention, a light scattering type sensor (hereinafter, referred to as a light sensor) may be used to measure the contamination state of the vacuum chamber. The light sensor may be disposed at a vent pipe of the vacuum apparatus, through which the particles are discharged. A light generated by the light sensor is radiated to the particles, and the light sensor may detect the light scattered by the particles, and thus the contamination level of the vacuum chamber can be measured. The light generated by the light sensor may be radiated into the vent pipe by an optical window.

However, as the particles are adsorbed and deposited on the optical window, the light cannot be radiated into the vent pipe. Accordingly, the optical window should be replaced periodically. The optical window is very expensive compared to the crystal vibrator, so the maintenance cost may increase. Additionally, the light sensor is usually disposed in the vent pipe, not inside the vacuum chamber, because the light sensor is relatively big in size. Thus, the vent pipe should have the shape corresponding to the size of the light sensor.

However, since the particle detector P_D according to the exemplary embodiment of the present invention includes the crystal vibrator having a size relatively smaller than that of the light sensor, the particle detector P_D may be disposed inside the vacuum chamber 10 regardless to the space inside the vacuum chamber 10.

When the particles are adsorbed to the surface of the crystal vibrator and form stack of particles having predetermined thickness, the crystal vibrator may be replaced. That is, when the frequency of the crystal vibrator is decreased from the amount of the particles stacked on the surface of the crystal vibrator under a reference frequency of the crystal vibrator, the crystal vibrator may be replaced with a new crystal vibrator. The crystal vibrator is cheaper than the optical window. Accordingly, the maintenance cost of the particle detector P_D may be reduced.

Consequently, the vacuum apparatus 100 may measure the contamination state inside the vacuum chamber 10 using the particle detector P_D that is disposed inside the vacuum chamber 10 and have reduced maintenance cost.

In the exemplary embodiment of the present invention, the vacuum apparatus 100 that performs the deposition process has been described as a representative example, but the process performed in the vacuum apparatus 100 is not limited to the deposition process. That is, the exemplary configuration of the vacuum apparatus 100 may be used to perform various processes, such as a sputtering process, a chemical vapor deposition process, an etching process, etc.

For instance, the vacuum apparatus configured to perform the sputtering process, the chemical vapor deposition process, and the etching process may also include the vacuum chamber 10 that includes the particle detectors P_D shown in FIG. 1. The vacuum apparatus for the sputtering process, the chemical vapor deposition process, and the etching process may measure the contamination state inside the vacuum chamber 10 by using information about the pressure in the vacuum chamber 10 and the absorption amount of the particles sensed by the first and second sensor units SU1 and SU2.

Figure 4:
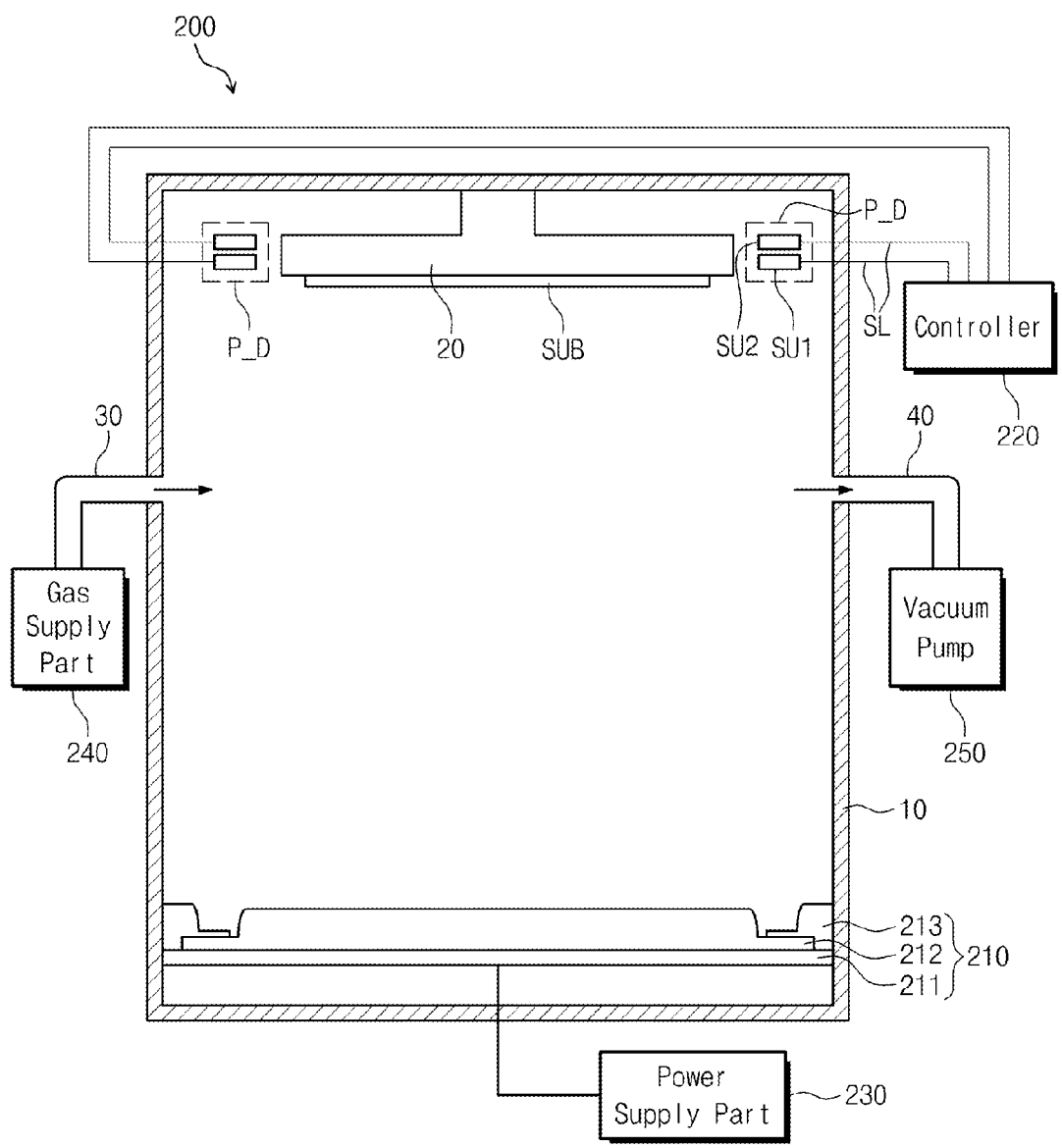
FIG. 4 is a cross sectional view showing a vacuum apparatus according to another exemplary embodiment of the present disclosure.

Hereinafter, the vacuum apparatus configured to perform the sputtering process will be described in detail with reference to FIG. 4. FIG. 4 is a cross sectional view showing a vacuum apparatus 200 according to another exemplary embodiment of the present disclosure.

Referring to FIG. 4, the vacuum apparatus 200 includes a vacuum chamber 10, a substrate SUB, a target part 210, a controller 220, a power supply part 230, a gas supply part 240, and a vacuum pump 250. According to the exemplary embodiment of the present in invention illustrated in FIG. 4, the vacuum apparatus 200 may be configured to perform a sputtering process.

The substrate SUB is fixed to the upper portion inside the vacuum chamber 10 by a substrate support portion 20. The target part 210 is disposed at the lower portion inside the vacuum chamber 10 facing the substrate SUB.

The target part 210 includes a first supporter 211, a sputtering target 212, and a second supporter 213. The sputtering target 212 is supported by first and second supporters 211 and 213. In detail, the first supporter 211 is attached to a lower surface of the sputtering target 212 to support the sputtering target 212. The second supporter 213 is attached to side surfaces and left and right portions of the upper surface of the sputtering target 212 to support the sputtering target 212.

The sputtering target 212 is disposed with the upper surface facing the substrate SUB. The left and right portions of the sputtering target 212 may have a thickness thinner than that of a center portion thereof.

The sputtering target 212 is formed of a material to be deposited onto the substrate SUB. For instance, the sputtering target 212 may include aluminum (Al), aluminum alloy, or an equivalent thereof. The sputtering target 212 may also be formed of indium tin oxide (ITO), indium zinc oxide (IZO), indium oxide (IO), ZnO, tin zinc oxide (TZO), AZO, GZO, or an equivalent thereof.

The power supply part 230 may include a RF power source or a DC power source. The power supply part 230 may apply the RF power source or the DC power source to the sputtering target 212. The power supply part 230 is electrically connected to the sputtering target 212 through the first and second supporters 211 and 213. Accordingly, the power supply part 230 may apply the power source to the sputtering target 212 through the first and second supporters 211 and 213.

The power supply part 230 applies a negative (−) power source to the sputtering target 212 so that the sputtering target 212 may be configured to operate as a cathode electrode. The negative (−) power source is applied to the sputtering target 212 through the first supporter 211 and the second supporter 213. The vacuum chamber 10 may be configured to operate as an anode electrode.

The gas supply part 240 provides rare gases, e.g., argon (Ar), into the vacuum chamber 10 through a gas supply pipe 30. The gas supply part 240 includes inert gas such as argon, krypton, helium, xenon, etc. These gases collide with the sputtering target 212, and thus the sputtering material is ejected from the sputtering target 212.

The gas supply part 240 may also provide a reactive gas including at least one of oxygen-containing gas and one or more nitrogen-containing gas. The reactive gas reacts with the sputtering material to form a layer on the substrate. That is, when the layer formed on the substrate SUB is an oxide material with oxygen, the argon gas is provided into the vacuum chamber 10 with oxygen gas.

The gas used to perform the sputtering process and a by-product generated during the sputtering process may be discharged from the vacuum chamber 10 through a discharge pipe 40. The discharge pipe 40 is connected to the vacuum pump 250, e.g., a cryogenic pump. The vacuum pump 250 maintains the vacuum chamber 10 in a low pressure vacuum state.

The particle detector P_D has the same structure and function as those of the vacuum apparatus 100 shown in FIG. 1, and thus the details thereof will be omitted.

The light sensor described above may only be disposed in the discharge pipe 40 since the size of the light sensor is generally too big to be disposed inside the vacuum chamber 10. However, the particle detector P_D according to the exemplary embodiment of the present invention may be disposed inside the vacuum chamber 10.

When the negative (−) electric potential is applied to the sputtering target 212 from the power supply part 230, electrons are emitted from the sputtering target 212. The electrons emitted from the sputtering target 212 collide with gas particles of the gas introduced into the vacuum chamber 10. The gas particles are ionized by glow discharge plasma generated from the collision of the electrons and the gas particles.

The ionized gas particles, e.g., positive (+) ion particles, are accelerated toward the sputtering target 212 and collide with the sputtering target 212. The sputtering material ejected from the sputtering target 212 from the collision of the ionized gas particles and the sputtering target 212 is deposited onto the substrate SUB. The sputtering material deposited on the substrate SUB may be defined as the deposition material.

The sputtering materials that are not deposited on the substrate SUB may correspond to the particles as the contamination materials. The first sensor units SU1 are disposed facing the deposition direction of the particles. Therefore, the particles may be provided to the first sensor units SU1 of the particle detectors P_D disposed adjacent to the substrate SUB.

The first sensor units SU1 sense the pressure in the vacuum chamber 10 and the absorption amount of the particles. The second sensor units SU2 sense the pressure in the vacuum chamber 10.

The information about the pressure in the vacuum chamber 10 and the absorption amount of the particles sensed by the first sensor units SU1 and the information about the pressure in the vacuum chamber 10 sensed by the second sensor units SU2 are provided to the controller 220. The controller 220 converts the information about the pressure in the vacuum chamber 10 and the absorption amount of the particles sensed by the first sensor units SU1 to a first data and converts the information about the pressure in the vacuum chamber 10 sensed by the second sensor units SU2 to a second data. The controller 220 subtracts the second data from the first data to generate a third data. The controller 220 analyzes the contamination state in the vacuum chamber 10 using the third data. Consequently, the vacuum apparatus 200 may monitor the particles generated during the vacuum process and measure the contamination state in the vacuum chamber 10 in real time.

Figure 5:
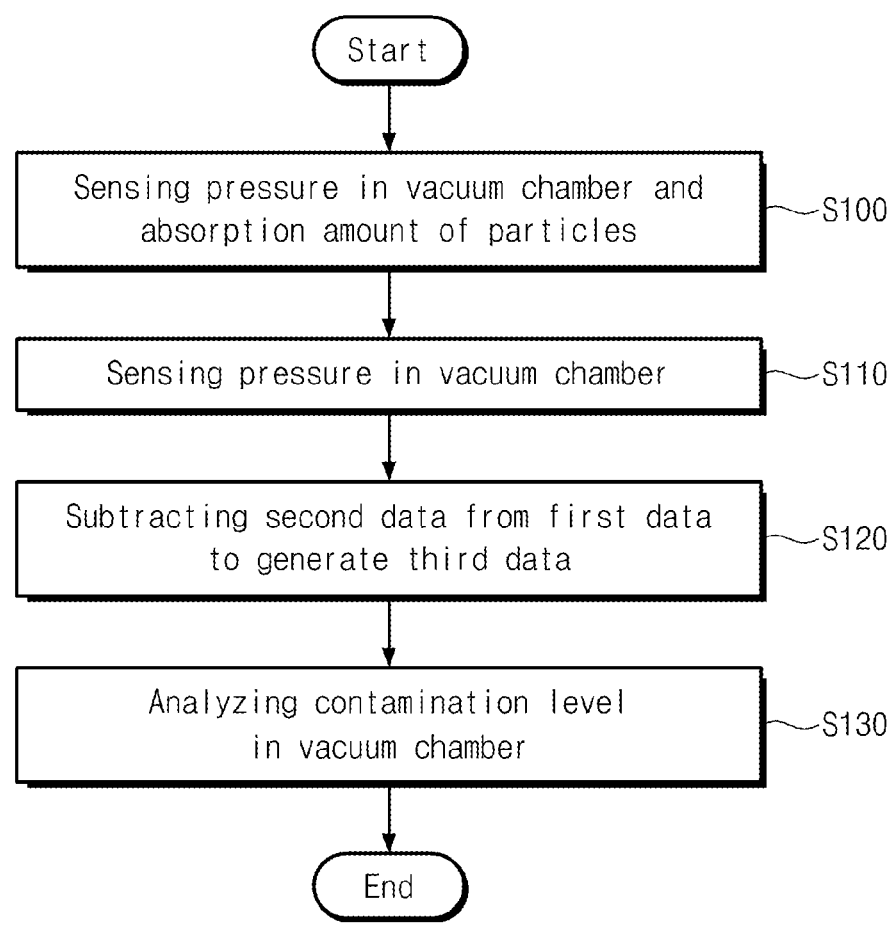
FIG. 5 is a flowchart showing a monitoring method of a vacuum apparatus according to an exemplary embodiment of the present disclosure.

FIG. 5 is a flowchart showing a monitoring method of the vacuum apparatus according to an exemplary embodiment of the present disclosure.

Referring to FIG. 5, the pressure of the vacuum chamber 10 and the absorption amount of the particles adsorbed to the first sensor units SU1 are sensed by the first sensor units SU1 (S100).

In detail, the frequency of the first sensor S1 of each of the first sensor units SU1 may be changed by the pressure in the vacuum chamber 10 and the absorption amount of the particles. The change in frequency of the first sensor S1 is sensed, and the information about the change in frequency of the first sensor S1 is provided to the controller 120 (S100).

The pressure in the vacuum chamber 10 is sensed by the second sensor units SU2 (S110). In detail, the frequency of the second sensor S2 of each of the second sensor units SU2 may be changed by the pressure in the vacuum chamber 10. The change in frequency of the second sensor S2 is sensed and the information about the change in frequency of the second sensor S2 is provided to the controller 120 (S110).

The third data is generated by subtracting the second data about the pressure in the vacuum chamber 10 sensed by the second sensor units SU2 from the first data about the pressure in the vacuum chamber 10 and the absorption amount of the particles sensed by the first sensor units SU1 (S120).

In detail, the change in frequency of the first sensor S1 is converted to the first data by the controller 120 and the change in frequency of the second sensor S2 is converted to the second data by the controller 120. The controller 120 subtracts the second data from the first data to generate the third data. The third data has the value corresponding to the absorption amount of the particles (S120).

The contamination level of the vacuum chamber 10 is analyzed on the basis of the third data (S130). The controller 120 determines that the contamination level is high when the value of the third data greater than a reference or threshold value.

Consequently, the vacuum apparatus 200 may monitor the particles generated during the vacuum process and measure the contamination state in the vacuum chamber 10 in real time.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. A vacuum apparatus, comprising:
   a vacuum chamber;
   first sensor units disposed in the vacuum chamber facing a deposition direction of particles; and
   second sensor units disposed in the vacuum chamber, each disposed on a corresponding first sensor of the first sensor units facing away from the deposition direction,
   wherein the first sensor units are configured to sense a pressure in the vacuum chamber and an absorption amount of the particles adsorbed to the first sensor units,
   wherein the second sensor units are configured to sense the pressure in the vacuum chamber,
   wherein each of the first sensor units comprises:
      a first sensor case; and
      a first sensor disposed on the first sensor case facing the deposition direction, and
   wherein each of the second sensor units comprises:
      a second sensor case; and
      a second sensor disposed on the second sensor case facing away from the deposition direction.

2. The vacuum apparatus of claim 1, further comprising:
   a substrate disposed at an upper portion in the vacuum chamber; and
   a deposition material disposed at a lower portion in the vacuum chamber, particles of the deposition material to be provided onto the substrate in the deposition direction,
   wherein the at least a portion of the particles of the deposition material are not deposited onto the substrate.

3. The vacuum apparatus of claim 2, wherein the first sensor units and second sensor units are disposed adjacent to a side surface of the substrate.

4. The vacuum apparatus of claim 1, wherein each of the first sensor units further comprises
   a first sensor fixture,
   wherein the first sensor case is disposed on the first sensor fixture, and
   wherein the first sensor is configured to sense the pressure in the vacuum chamber and the absorption amount of the particles adsorbed to the first sensor.

5. The vacuum apparatus of claim 4, wherein each of the second sensor units further comprises
   a second sensor fixture,
   wherein the second sensor case is disposed on the second sensor fixture, and
   wherein a rear surface of the second sensor fixture, which opposes a surface of the second sensor fixture on which the second sensor case is disposed, is disposed facing a rear surface of the first sensor fixture, which opposes a surface of the first sensor fixture on which the first sensor case is disposed, and
   wherein the second sensor is configured to sense the pressure in the vacuum chamber.

6. The vacuum apparatus of claim 5, wherein the first sensor and second sensor each comprise a crystal vibrator.

7. The vacuum apparatus of claim 6, wherein:
   a frequency of the first sensor is configured to change according to the pressure in the vacuum chamber and the absorption amount of the particles adsorbed to the first sensor; and
   a frequency of the second sensor is configured to change according to the pressure in the vacuum chamber.

8. The vacuum apparatus of claim 7, further comprising a controller that is configured to receive information about the change in the frequency of the first sensor and information about the change in the frequency of the second sensor and configured to calculate the absorption amount of the particles.

9. The vacuum apparatus of claim 8, wherein the controller is configured to convert the information about the change in the frequency of the first sensor to a first data, convert the information about the change in the frequency of the second sensor to a second data, and subtract the second data from the first data to generate a third data.

10. The vacuum apparatus of claim 9, wherein the third data has a value corresponding to the absorption amount of the particles.

11. The vacuum apparatus of claim 1, wherein the vacuum chamber is configured to perform at least one of a deposition process, a sputtering process, a chemical vapor deposition process, and an etching process.

12. A method of monitoring particles in a vacuum apparatus, comprising:
   sensing, by first sensor units, a pressure in a vacuum chamber and an absorption amount of the particles adsorbed to the first sensor units, the first sensor units disposed in the vacuum chamber facing a deposition direction of the particles;
   sensing, by second sensor units, the pressure in the vacuum chamber, the second sensor units disposed in the vacuum chamber facing away from the deposition direction and disposed on corresponding first sensor units; and
   analyzing a contamination level of the vacuum chamber,
   wherein each of the first sensor units comprises:
      a first sensor case; and
      a first sensor disposed on the first sensor case facing the deposition direction, and
   wherein each of the second sensor units comprises:
      a second sensor case; and
      a second sensor disposed on the second sensor case facing away from the deposition direction.

13. The method of claim 12, wherein the vacuum apparatus further comprises:
   a substrate disposed at an upper portion in the vacuum chamber; and
   a deposition material disposed at a lower portion in the vacuum chamber, particles of the deposition material to be provided onto the substrate in the deposition direction, and
   wherein the at least a portion of the particles of the deposition material are not deposited onto the substrate, and the first sensor units and second sensor units are disposed adjacent to a side surface of the substrate.

14. The method of claim 12, wherein each of the first sensor units further comprises
   a first sensor fixture, wherein the first sensor case is that disposed on the first sensor fixture, and wherein the first sensor comprises a crystal vibrator, and the first sensor is configured to sense the pressure in the vacuum chamber and the absorption amount of the particles adsorbed to the first sensor.

15. The method of claim 14, wherein each of the second sensor units further comprises a second sensor fixture, wherein the second sensor case is disposed on the second sensor fixture, wherein the second sensor comprises the crystal vibrator, wherein a rear surface of the second sensor fixture, which opposes a surface of the second sensor fixture on which the second sensor case is disposed is disposed facing a rear surface of the first sensor fixture, which opposes a surface of the first sensor fixture on which the first sensor case is disposed, and wherein the second sensor is configured to sense the pressure in the vacuum chamber.

16. The method of claim 15, wherein the sensing the pressure in the vacuum chamber and the absorption amount of the particles comprises:

sensing a frequency of the first sensor, wherein the frequency of the first sensor is configured to change according to the pressure in the vacuum chamber and the absorption amount of the particles adsorbed to the first sensor; and outputting the change in frequency of the first sensor.

17. The method of claim 16, wherein the sensing the pressure in the vacuum chamber comprises:

sensing a frequency of the second sensor, wherein the frequency of the second sensor is configured to change according to the pressure in the vacuum chamber; and outputting the change in frequency of the second sensor.

18. The method of claim 17, wherein the analyzing a contamination level of the vacuum chamber comprises:

converting the change in frequency of the first sensor to the first data;

converting the change in frequency of the second sensor to the second data; and subtracting the second data from the first data to generate a third data, wherein the third data corresponds to the absorption amount of the particles.

19. The method of claim 18, wherein the analyzing of the contamination level of the vacuum chamber further comprises determining that the contamination level is high when the value of the third data is greater than a reference value.

* * * * *